(12) United States Patent
Jackson

(10) Patent No.: US 6,261,288 B1
(45) Date of Patent: Jul. 17, 2001

(54) IMPLANT STABILIZATION AND LOCKING SYSTEM

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 0 days.

(21) Appl. No.: 09/500,297

(22) Filed: Feb. 8, 2000

(51) Int. Cl.[7] .................................................. A61B 17/58
(52) U.S. Cl. ................................................ 606/61; 606/72
(58) Field of Search .................................. 606/61, 60, 59, 606/72, 73, 53; 403/362, 382, 394

(56) References Cited

U.S. PATENT DOCUMENTS

| | | |
|---|---|---|
| 4,763,644 | 8/1988 | Webb . |
| 5,005,562 | 4/1991 | Cotrel . |
| 5,127,912 * | 7/1992 | Ray et al. ............................. 606/61 |
| 5,147,360 | 9/1992 | Dubousset . |
| 5,382,248 | 1/1995 | Jacobson et al. . |
| 5,476,463 * | 12/1995 | Boachie-Adjei et al. ............. 606/61 |
| 5,643,260 | 7/1997 | Doherty . |
| 5,697,929 | 12/1997 | Mellinger . |
| 5,716,355 * | 2/1998 | Jackson et al. ....................... 606/61 |
| 5,980,523 * | 11/1999 | Jackson ................................. 606/61 |
| 6,136,003 * | 10/2000 | Hoecket et al. ...................... 606/61 |

FOREIGN PATENT DOCUMENTS

WO 94/10927   5/1994   (WO) .

* cited by examiner

*Primary Examiner*—Pedro Philogene
(74) *Attorney, Agent, or Firm*—John C. McMahon (57) ABSTRACT

A medical implant including at least one rod and an anchor for resisting both axial and angular movement of the rod relative to the anchor. The anchor includes a set screw that simultaneously biases the rod against a rod receiving wall of the anchor while also having threads that cut into a surface of the rod to help resist relative rotation. The anchor also includes a pair of bone screws that are laterally spaced relative to each other and at least one bone screw is laterally spaced relative to the rod to resist torsion and to secure the implant against dislodgement.

11 Claims, 5 Drawing Sheets

IMPLANT STABILIZATION AND LOCKING SYSTEM

BACKGROUND OF THE INVENTION

The present invention is directed to an implant and a configuration for implantation of the implant into the human body, especially along the spine, having improved stabilization and locking with respect to desired position of the overall implant, as well as improved resistance to torsion during use.

The art of correcting back deformities, injuries and the like has advanced dramatically in recent years. Surgeons who perform operations on the spine and related bones of the body are constantly developing new procedures and techniques that require implants which are capable of being stable in the body after implantation and which firmly lock in place so as to resist the substantial pressures and forces developed by the body on the implant. Such implants must often also resist twisting or torsion applied to parts of the implant and prior art implants have not always been successful at resisting twisting or torsion.

Such implants often involve rods which are placed along the spinal column or various bones of the living body and, once secured to the bones, such rods may be bent and shaped to force the bones to align with the rods and, in this manner, either provide correction to the bones caused by deformity, injury or the like. That is, one or more rods are placed in the correct curvature for the spine and the spinal bones are joined to the rod or rods, before or after bending the rods, in such a manner as to thereafter force the bones to follow the same configuration as the rods. Once the rods are bent, forces created by the muscles of the patient, or by sudden movement, or by accident, or the like often act to try to rotate or apply torque to the implant as a whole or a rod individually. That is such forces generally apply torsion to the apparatus. Such torsion may act to loosen or even dislodge the implant or to turn or rotate one or more rods to a less effective support position. It is desirable that the apparatus be able to resist such forces acting upon it.

Historically, the rods used as implants in the manner described above, are typically joined with various bones along the length of the rod by use of bone screws or other implants that are joined with the rod. It has been found that conventionally available implants have systems that join rods to bone screws or intermediate connectors in such a manner that the rods are often held against axial movement relative to the bone screws or intermediate connector. That is, the rods are not likely to move substantially with respect to the other implants in a direction that is along the central axis of the rod. However, because of the substantial forces exerted on the rod during use, certain forces act to try to rotate the rod within bone screws and connectors, such that the spinal corrective configuration and positioning of the rod can slip due to rotation of the rod from an optimal position to one that is less suited for the patient. This can occur when substantial forces are applied to the back during exercise, accident or the like.

Consequently, it is desirable to have an implant that not only effectively resists axial movement of the rod relative to the other implants, but also effectively resists torque or torsion that produce turning of the rod or rotation of the rod relative to the implants. One use of the present invention is especially suited for the locking and stabilizing an anterior spinal implant. In particular, the installation of anterior spinal rods is often utilized to reposition the spine and correct deformities and the like. Such a rod is typically anchored at opposite ends to vertebrae and is likewise joined with vertebrae along the length of the rod by bone screws or the like. Such a system is typically installed by curving the rod to fit the malformed spine of the patient and then securing the anchors at both ends and various intermediate bone screws to the rod. The rod is thereafter bent by rod benders to assume the desired configuration of the spine and the rod in this manner translates the various bones of the spine along with it to the correct configuration.

Once the rod is bent, the body exerts a substantial amount of rotational force or torsion on the rod, especially should the patient be struck on the back, during exercising, or the like. It is also noted that the rod can first be bent and then the bone moved to the rod and secured to the rod. In either case, it is important that the anchors at opposite ends of the rod resist rotation of the rod therein and that the anchors themselves remain stable and securely attached to an associated bone. Furthermore, it is important to both lock the rod against rotation in or relative to the bone screw and to secure the anchors of the rod against rotation relative to the spine.

An implant system is therefore desirable that provides a strong anchor at opposite ends of the rod that resists rotation of the rod both relative to the bone screws and relative to the spine during procedures at the time of implantation and later during use.

SUMMARY OF THE INVENTION

A medical implant apparatus is provided which includes an anchor for operatively resisting rotation or dislodgement of the implant apparatus and also operatively resists rotation of a spinal implant rod associated with the apparatus relative to bone screws and other elements of an implant system. The invention is especially useful in conjunction with rods that are utilized to correct deformities, injuries or the like in the spine, but has related applications in other types of implants.

In particular, an anchor is provided for securing a rod to bone in a living person, especially near the end of the rod. The anchor has a first bone screw to which the rod is attached. The rod may be attached to the first bone screw either directly or indirectly through another implant. The bone screw may be an open bone screw that has a yoke that is closed by a cap once the rod is placed in the yoke, or may be a closed bone screw where the rod is received through an opening in the top of the bone screw.

The anchor further includes a second bone screw which is positioned radially out or laterally with respect to the first bone screw. The second bone screw is also connected either directly or indirectly to the rod and is typically joined by an offset or lateral implant to the rod. In this manner, the first and second bone screws are positioned laterally with respect to each other or generally in a line that is perpendicular or radially outward with respect to the axis of the rod and thus cooperate to provide greater resistance to rotation of the rod, both because there are multiple bone screws secured to the rod at this location and because there is a lever arm that is provided between the two bone screws to resist rotation or torsion of the rod due to action of the body or outside forces.

Secondly, a set screw in conjunction with optimal positioning and configuration for the set screw is likewise provided to resist rotation of the rod. In particular, the rod is positioned and secured in a bore or other opening that receives the rod by a set screw that resists both axial movement of the rod and rotational movement of the rod within the opening. This is accomplished by effective positioning of the set screw relative to the rod and the opening. In particular, the set screw is positioned such that as the set screw is installed, the set screw first urges the rod against an opposed wall of the bore or opening in such a manner that the rod is held against that wall and secured between the set screw and the wall. In this manner, the rod is frictionally secured in the opening, especially where the opening is not fully enclosed; for example, in the situation where the implant has a hook connection with the rod. Thus, in part, the set screw and friction against the wall of the bore resist axial movement of the rod relative to the remainder of the implant.

The implant may include additional set screws that secure the rod against axial movement and this is especially true in the situation where the implant includes the above-noted anchor wherein at least one bone screw of the anchor is secured by a set screw which passes radially against the rod to resist axial movement. However, a second aspect of the present invention is a screw that may be used with one or both bone screws wherein such a set screw is angled and positioned during installation so that threads of the set screw engage the rod just inward of a tangent of the rod subsequent to the rod being urged fully against an opposite wall by the head or front of the set screw. That is, the set screw passes along the side of the rod opposite the wall and the threads of the set screw actually cut into the rod to a sufficient depth to provide substantial frictional, as well as mechanical penetration, engagement to resist rotation or torsion of the rod within the bone screw opening or bore.

Where the rod is received in a circular bore, the set screw preferably engages the rod somewhat inward of tangential engagement so as to cut into the rod. In the situation where the rod is received in an opening having a hook or the like, it may be necessary to angle the set screw slightly so that as the set screw is advanced, the set screw not only pushes the rod against the opposed wall, but also slightly upward into the upper wall away from the open mouth of the hook and thus locks the rod in the opening, resists axial movement of the rod and resists subsequent rotation of the rod relative to the anchor by cutting into the rod with the threads thereof.

While it is foreseen that the present invention may be used in a wide variety of different medical implants, it is especially suited for the situation where an anterior spinal rod is placed within the patient and joined to various vertebrae by anchors at opposite ends thereof that have bone screws imbedded in vertebrae of the spine of the patient. The spinal rod is then manipulated by benders to adjust the curvature of the spine and the anchors both secure the rod against axial movement and rotational movement relative to the location where the rod joins the anchors and through the anchors is secured to the spine.

The invention may also be used in other types of implants, such as lateral connectors where a connector joins two rods on opposite sides of the vertebrae to hold the rods in place. Such connectors are often joined to the rods by hooks which are susceptible to both slippage and rotation. The set screw and set screw positioning of the present invention both locks the rod within the hook and resists rotation of the rod within the hook.

OBJECTS AND ADVANTAGES OF THE INVENTION

Therefore, the objects of the present invention are: to provide an implant system including an apparatus for use in conjunction with correcting deformities, injuries and the like with respect to the human spine or other bones wherein a rod is implanted along bone and wherein the apparatus resists rotation of the rod once the implant is complete and firmly anchors the rod within the overall system to the bone; to provide such an implant system that is adaptable to rods utilized for many purposes, including anterior spinal systems, connectors utilized in joining together parallel rods or the like; to provide such a system having an anchor that operably connects to and secures a rod to a bone; to provide such a system wherein the anchor includes two separate bone screws that are spaced radially apart from one another and at least one of the bone screws is spaced laterally, preferably radially, with respect to the rod and wherein the bone screws are both joined to the rod in such a manner as to provide resistance to both rotation and axial slippage of the rod at the anchor; to provide such a system wherein a set screw is further provided that is designed, configured and positioned in the implant apparatus to resist rotation of the rod; to provide such a set screw and apparatus that operably allows the set screw to be positioned along the rod in such a manner that the threads of the set screw cut into the rod and thereafter resist rotation of the rod; to provide such a system wherein the set screw is positioned relative to the rod so as to also urge the rod against an opposite wall, especially an arcuate wall of a bore or opening that receives the rod; to provide such a set screw which abuts and cuts into the rod just radially inward of a position where the set screw would be tangential to the rod; and to provide such an apparatus that is easy to use, comparatively simple to manufacture and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Illustrated in FIGS. 1 through 6 is a spinal implant system or apparatus in accordance with the present invention and generally represented by the reference numeral 1. The spinal implant system 1 is illustrated positioned in association with a spine 4 which is shown without surrounding tissue in order to better illustrate the invention. Normally the system 1 would be used in a living human. The spinal system 1 is also illustrated being manipulated by a set of benders 6 and 7 in FIGS. 1 and 2.

Figures 1, 2, 3:
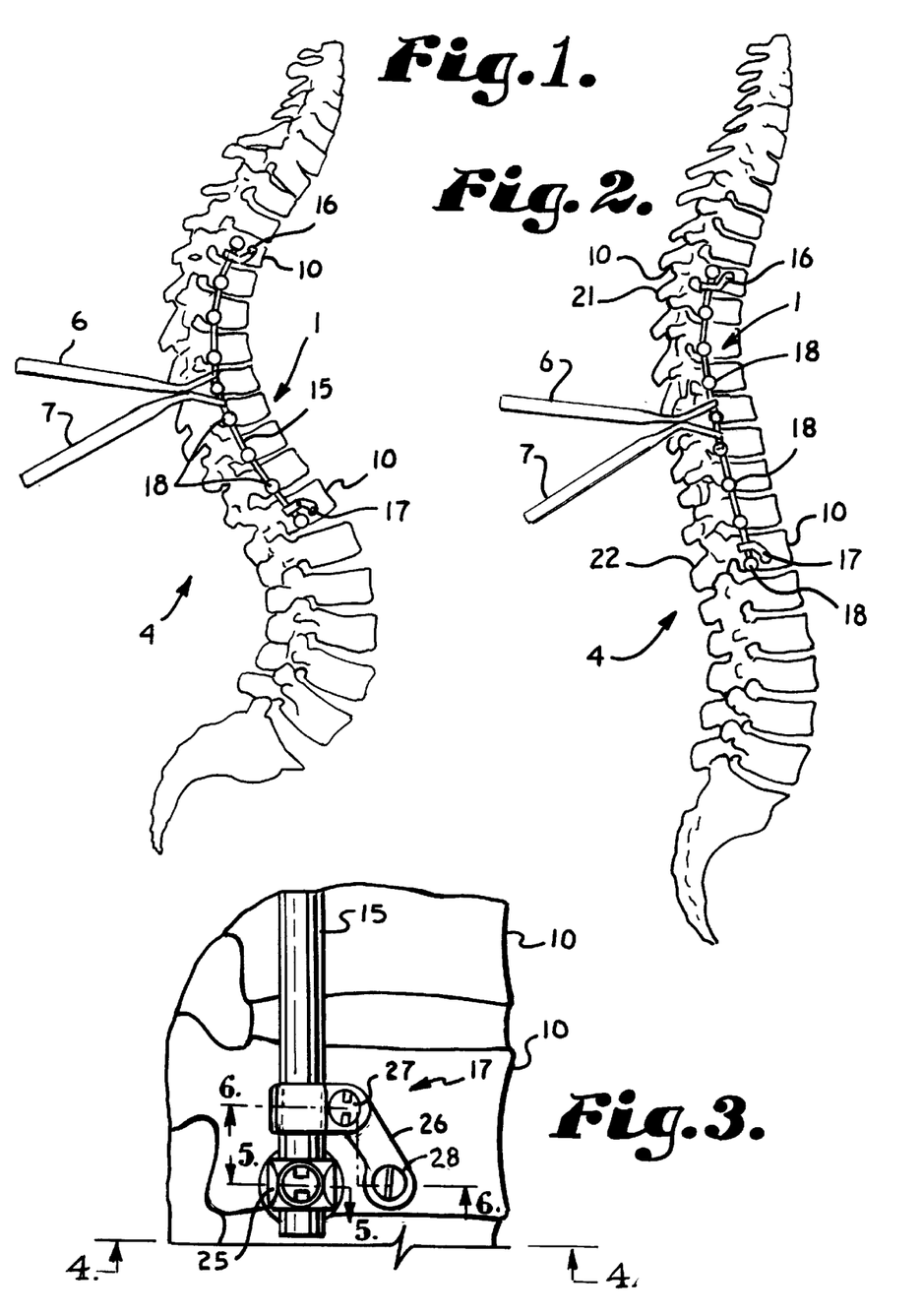
FIG. 1 is a side view of a spine which is shown without the remaining body for purposes of illustration, showing an implant system in accordance with the present invention, including a rod and anchors for securing the rod on opposite ends thereof to the spine and a pair of benders positioned to bend the rod.
FIG. 2 is a side elevational view of the spine of FIG. 1 showing the implant system and the spine subsequent to bending of the rod by the benders.
FIG. 3 is an enlarged and fragmentary front view of the spine, the rod and one of the anchors.

In the embodiment illustrated in FIGS. 1 through 6, the spine 4 includes a series of vertebrae 10 that sit adjacent to one another and which are joined together in such a manner as to form the overall spine 4. In FIG. 1, the spine 4 has improper curvature due to congenital deformity, age-related processes, injury or the like. In the illustrated usage, it is desirable to modify the configuration of the spine 4 from the configuration shown in FIG. 1 to the configuration shown in FIG. 2 for medical reasons.

The spinal implant system 1 generally includes an elongate rod 15, an upper anchor 16, a lower anchor 17, and a series of bone screws 18. The illustrated rod 15 is a conventional rod utilized in many types of back surgery and the like for providing support or positioning relative to the spine 4 or other bones. The illustrated rod 15 is constructed of stainless steel and has a smooth exterior with a circular cross section. However, it is foreseen that other types of rods constructed of other types of material and having full or partial roughened or knurled surfaces may also be utilized in conjunction with the invention.

The bone screws 18 are of a conventional type and may be either closed bone screws which have an enclosed top or open bone screws, which have an open top that is subsequently closed by a closure after the rod 15 is inserted. That is, the open bone screws will typically have an upper yoke which receives the rod 15 and which is closed by a cap or closure that are conventional in type and not specifically illustrated herein.

The upper and lower anchors 16 and 17 both incorporate many of the aspects of the present invention and are quite similar in nature with the exception of being mirror images of one another and with the exception of being secured to an upper anchor vertebra 21 and a lower anchor vertebra 22, respectfully. Consequently, while only the lower anchor 17 will be described in detail, the same description also applies to upper anchor 16.

In particular, attention is directed to FIG. 3 which shows the anchor 17 in greater detail. The anchor 17 includes a first bone screw 25, an offset or lateral bone screw support 26 having a locking set screw 27, and a second bone screw 28.

Figures 4, 5, 6:
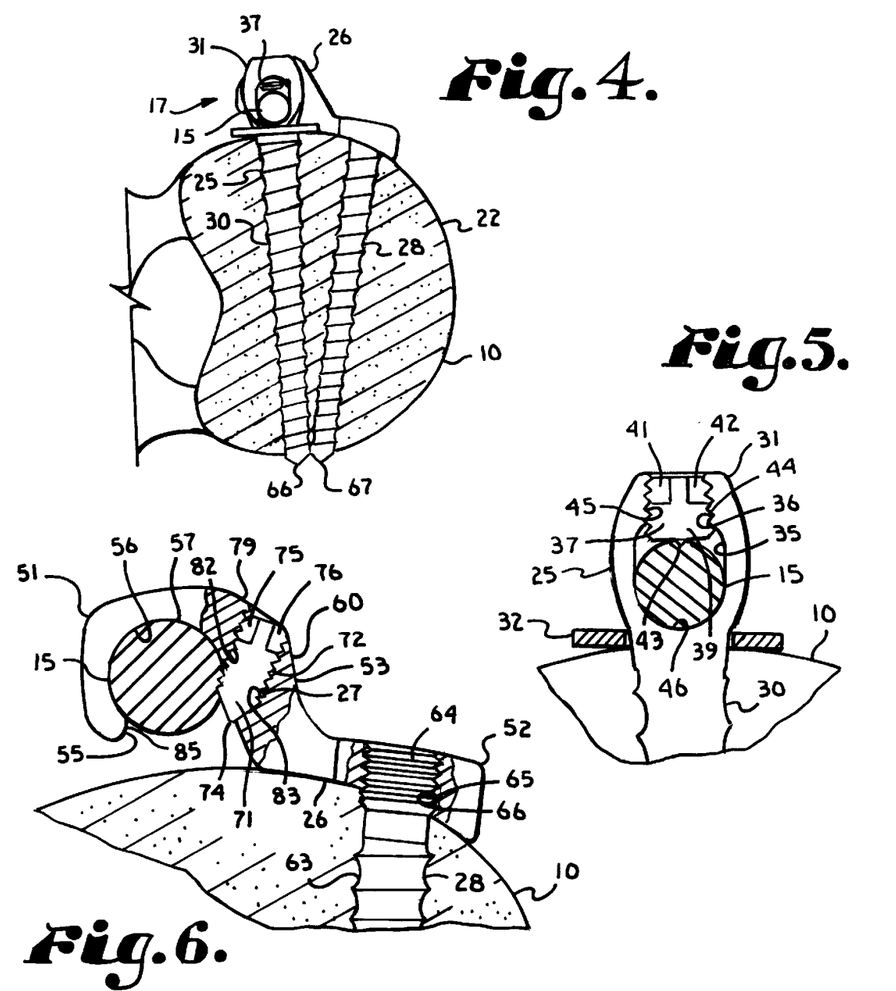
FIG. 4 is an enlarged cross-sectional view of the anchor of FIG. 3 shown mounted on a vertebra, taken along line 4—4 of FIG. 3.
FIG. 5 is an enlarged and fragmentary cross-sectional view of the anchor of FIG. 3, taken along line 5—5 of FIG. 3.
FIG. 6 is an enlarged and cross-sectional view of the anchor of FIG. 3 and associated vertebra, taken along line 6—6 of FIG. 3.

The first bone screw 25 has a conventional threaded screw shank 30 with a head 31. In use, such is as shown in FIG. 4, the shank 30 preferably passes into and through the lower anchor vertebra 22 while the head 31 extends outwardly from the vertebra 22. A structure that is generally a washer 32 is positioned between the head 31 and the shank 30 and against the vertebra 22 during use.

The head 31 of the illustrated first bone screw 25 is of a closed type having a bore 35 that is somewhat ovate in shape and which extends diagonally through the head 31. The bore 35 is sized and shaped to loosely receive the rod 15, as is seen in FIGS. 4 and 5.

The head 31 also includes a second bore 36 which is axially aligned with the shank 30 and which extends inwardly from the top of the head 31. The bore 36 receives a set screw 37 which may be of many different types. The illustrated set screw 37 is of a type having a break off head (not shown) that separates from a body 39 during installation.

The set screw 37 includes diametrically opposed removal slots 41 and 42 and a point 43 that is positioned and shaped to frictionally engage, as well as slightly penetrate radially with respect to a central axis of the rod 15, the rod 15 during advancement of the set screw 37 in the bore 36. The set screw 37 has a radially positioned exterior threaded surface 44 which is received in a similarly threaded surface 45 of the bore 36. As is illustrated in FIG. 5, after installation the set screw 37 urges the rod 15 to be snugly received against a curved lower wall 46 opposite the set screw 37 so as to frictionally secure the rod 15 against axial movement.

The offset screw support 26 is perhaps best shown in FIGS. 3 and 6. The support 26 has a hook 51 at one end thereof and a bone screw receiver 52 at an opposite end thereof that are joined or connected by a slanted shoulder 53.

The hook 51 is sized and shaped to be received over the rod 15 as is shown in FIG. 6. The hook includes a lip 55 that encircles one side of the rod 15. The hook 51 has a rod receiving surface 56 that is sized and shaped to correspond with an outer surface 57 of the rod 15 and to receive the rod 15 snugly thereagainst. The shoulder 53 begins diagonally opposite the lip 55 and also receives a portion of the rod outer surface 57 thereagainst. The shoulder 53 is angled with respect to the hook 51 so that the shoulder 53 does not extend radially outward from the rod 15, but rather at a substantial angle with respect to the rod 15. An undersurface of the hook 51 and part of the shoulder 53 are shaped and positioned to rest upon the bone 10.

The shoulder 53 is fixedly secured to the bone screw receiver 52 and is sized, shaped and configured in conjunction with the hook 51 and the bone screw receiver 53, such that the second bone screw 28 is positioned radially or laterally and preferably radially outward from the first bone screw 25 in the manner shown in FIG. 3. That is, a line drawn through the middle of the first and second bone screws 25 and 28 would extend perpendicularly or radially with respect to the rod 15. The first bone screw 25 is spaced from the second bone screw 28, while both are mounted in the same anchor vertebra 22 and on the same side of the vertebra 22. The shoulder 53 has a sloped wall 60.

In the illustrated embodiment shown in FIGS. 1 through 6, the hook 51, set screw receiver 52 and shoulder 53 are all integral and commonly form the offset screw support 26, although it is foreseen that such a support could be formed with two or more independent elements.

The second bone screw 28 is of a type having a threaded shank 63 and a head 64 that has an outer threaded surface 65 that is received in a threaded bore 66 of the bone screw receiver 52. Preferably, the first bone screw 25 and second bone screw 28 are angled relative to one another in the vertebra 22 such that the heads 31 and 64 are spaced, but tips 66 and 67, respectively thereof, are located in close proximity to one another. This gives the bone screws 25 and 28 better strength to resist being pulled from the vertebra 22.

The offset screw support 26 is secured to the rod 15 by the set screw 27. The set screw 27 performs a number of different functions within the system 1. In particular, the set screw 27 has an elongate base 71 with a radially outward threaded surface 72. The set screw 27 also has a tip 74 and a pair of removal slots 75 and 76 that are located opposite the tip 74. Before installation, the set screw 27 may also have a break-away head (not shown, but of the type having reference numeral 327 in FIG. 15) that breaks away from the base 71 of the set screw 27 at a predetermined torque to allow the set screw 27 to be completely located beneath and to have a clean profile with respect to an upper surface 79 of the support 26, although it is foreseen that other types of set screws may be used in some embodiments of the invention.

The set screw 27 is received in a bore 82 that has an interior threaded surface 83 that is sized and shaped to threadably receive the set screw 27. The bore 82 is located in the side of the hook 51 opposite the lip 55 and partially within the shoulder 53. The position and angle of the bore 82 and consequently the location of the set screw 27 is important in allowing the set screw 27 to function in accordance with the invention.

In particular, as the set screw 27 advances in the bore 82, the set screw tip 74, which is pointed or has a truncated conical shape, initially engages the rod 15 and urges the rod 15 into snug engagement with the hook receiving surface 56. As the set screw 27 advances in the bore 82, the set screw 27 effectively blocks the opening 85 through which the rod 15 is received into the hook 51 at least sufficiently to prevent the rod 15 from coming away from the hook receiving surface 56. That is, the set screw 27 partially blocks the opening 85 to make the opening smaller than the cross-section of the rod 15. However, at the same time, the set screw 27 engages the rod 15 in such a manner that the set screw threaded surface 72 is slightly inward (toward the center or axis of the rod 15) of being tangential with respect to the rod outer surface 57. This allows the set screw threaded surface 72 to actually groove, cut or dig into the rod outer surface 57 and remain embedded or set therein in such a manner so as to highly resist rotation or torsion of the rod 15. That is, the set screw 27 both locks the rod 15 into the hook 51 resists axial movement of the rod 15 relative to the hook 51, while at the same time securing the rod 15 so as to highly resist rotation of the rod 15 within the hook 51.

While the set screw 37 and the first bone screw 25 also somewhat resist rotation of the rod 15, the comparatively small point contact of the set screw 37 with rod 15 is not highly effective at preventing rotation. However, the set screw 27, because of its position and threads on the side thereof actually cutting into the rod 15, is highly effective against preventing rotation. This is especially true when taken in combination with the set screw 37.

In use the upper anchor 16 and lower anchor 17 both secure the rod 15 to the upper anchor vertebra 21 and lower anchor vertebra 22, respectively, and resist movement of the rod 15 relative to the vertebra 21 and 22, both axially and rotationally relative to the rod 15. The set screw 27 especially resists rotation of the rod 15 within the anchors 16 and 17. Also, the upper anchor 16 and lower anchor 17 provide a pair of bone screws 25 and 26 that are spaced from one another and which are spaced along a line that extends perpendicularly outward from the rod 15 so as to provide a lever arm to further resist rotation of the anchors 16 and 17, as well as the associated rod 15, relative to the vertebrae 21 and 22 associated with the anchors 16 and 17. The two bone screws 25 and 28 also work in cooperation with each other to strengthen the anchors 16 and 17 with respect to their position in the anchor vertebrae 21 and 22.

The system 1 may be used in many different ways and with many different components. In the illustrated system 1, the various components are positioned within the spine 4, as has been noted above and as is shown in FIG. 1 with the rod 15 preformed into the curvature of the existing spine 4. After all of the components of the system 1 are in place and secured, the benders 6 and 7 are utilized to then bend the rod 15 to a new configuration, such as is shown in FIG. 2, which effectively modifies the configuration of the spine 4 to a new desired configuration.

During bending and subsequent to the final positioning of the spine 4, the rod 15 in conjunction with the anchors 16 and 17 hold the spine 4 in the desired position. The anchors 16 and 17 resist rotation of the rod 15 during the bending process and subsequently thereto at times when forces or stresses are applied to the vertebrae. This prevents the rod 15 from undesirably rotating within the remainder of the implant system or relative to the spine 4 during or subsequent to surgery.

As with subsequent embodiments, it is foreseen that the second bone screw 28 may be of the same type as the bone screw 25 where, in rare situations it is desirable to have a second rod receiving bone screw on the same side as and in close proximity to the bone screw 25, whereby a second rod or the like could be placed parallel to or in close proximity to the first rod 15.

Figures 7, 8, 9:
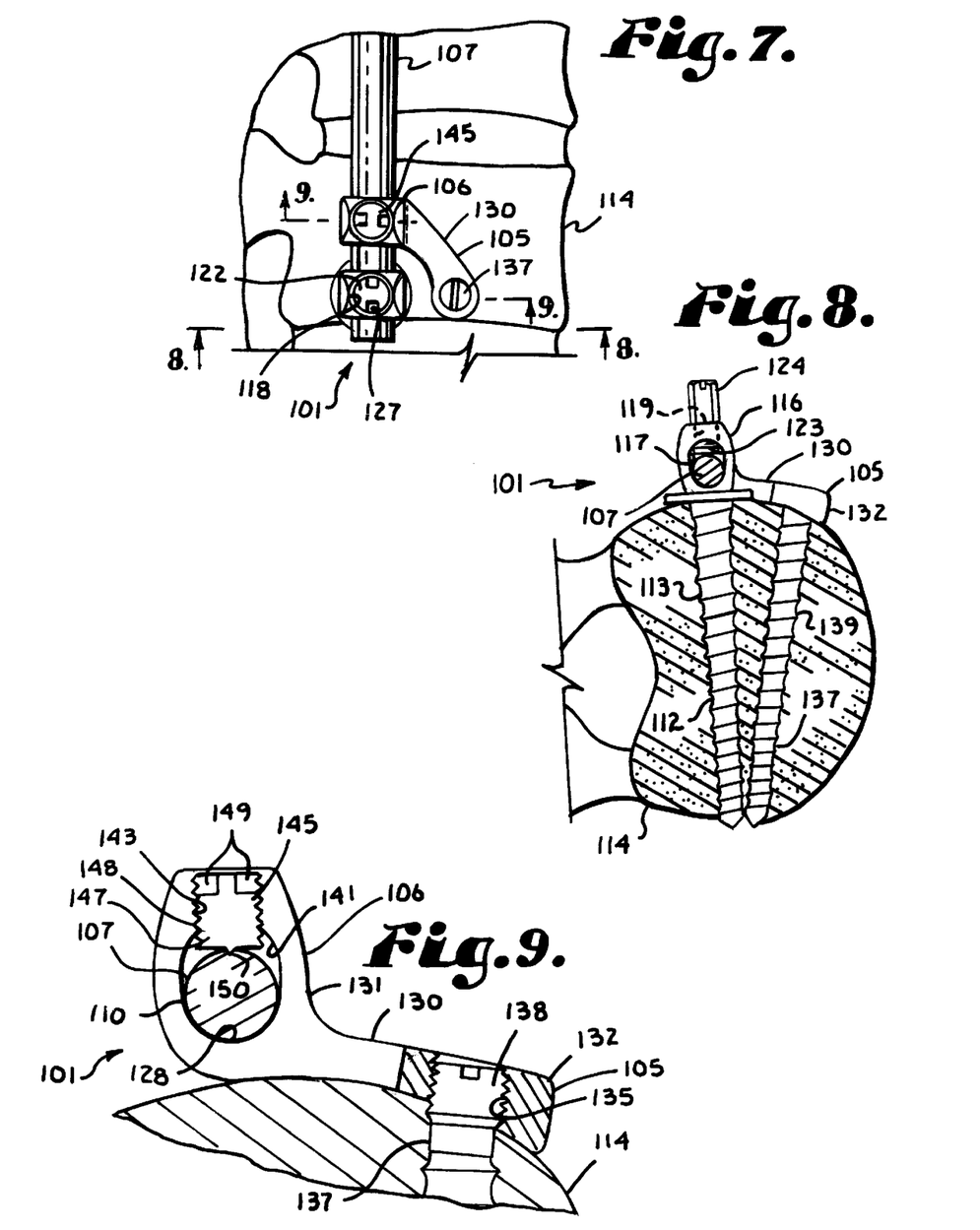
FIG. 7 is a fragmentary front elevational view of a first modified anchor in accordance with the present invention, in association with vertebrae and a rod.
FIG. 8 is a cross-sectional view of the first modified anchor, rod and associated vertebrae, taken along line 8—8 of FIG. 7.
FIG. 9 is an enlarged and cross-sectional view of the first modified anchor, associated vertebrae and rod, taken along line 9—9 of FIG. 7.

Illustrated in FIGS. 7 through 9 is a second embodiment of an implant system generally represented by the reference numeral 101. The implant system 101 is similar in many ways to the implant system 1 and, therefore, many repetitive parts will not be described in detail. The main difference between the implant system 101 and the implant system 1 is that the system 101 includes an offset or lateral connector 105 that has a closed head 106 for receiving the rod 107.

As is shown in FIG. 7, the implant system 101 includes an elongate rod 107 that has a curved outer surface 110 and is generally circular in cross-section. The implant system 101 also includes a first bone screw 112. As is shown in FIG. 8, the bone screw 112 has an elongate threaded portion 113 that is screwed into a vertebra 114 during use. The bone screw 112 also has a head 116 with an interior bore 117 that is generally perpendicularly aligned with respect to the threaded portion 113. The bore 117 is sized and shaped to be somewhat larger than the cross-section of the rod 107, so as to allow the rod 107 to be received within the bore 117. The bone screw head 116 also includes a second bore 118 that is generally axially aligned with the bone screw threaded portion 113 and which has an interior threaded wall 119. The bone screw bore 117 is somewhat larger than the rod 107.

A set screw 122 having a base 123 and a break-away head 124 is utilized to secure the position of the rod 107 relative to the bone screw 112. The head 124 is shown on the set screw 122 in FIG. 8, just prior to final torquing to a predetermined torque that causes the head 124 to separate from the base 123 exposing removal slots 127 that are seen in FIG. 7. In particular, the set screw 122 is received in the second bore 118 and advanced until it is urged against the rod 107 which in turn biases the rod 107 against the curved portion of the wall 128 of the bore 117 opposite the bore 118. The set screw base 123 is exteriorly threaded and received in a similar thread in the bore 118. As the set screw 122 advances against the rod 107, a torque is developed. As noted above, when the torque reaches a preselected level, the head 124 breaks away from the base 123 leaving the base 123 in the bore 118 and holding the rod 107 in position relative to the bone screw 112. The slots 127 become accessible from the top of the second bore 118 when the head 116 is broken away, as is seen in FIG. 7. The slots 127 may be utilized advantageously to receive a tool (not shown) for rotating the set screw 122 so as to provide removal of the set screw base 123 from the second bore 118.

The offset or lateral connector 105 also includes an offset arm 130 joined to the head 106 by a shoulder 131 and has a tail 132 opposite the head 106 that includes a bore 135. The bore 135 is interiorly threaded and receives a second bone screw 137 with an exteriorly threaded head 138 that threadably mates with the thread of the bore 135. The bone screw 137 also includes a lower portion 139 that is threadably received into the vertebra 114 at a spaced location from whereat the bone screw 113 is received into the bone 114 and, in particular, is laterally offset from whereat the bone screw head 116 is located. Preferably, the bone screw threaded lower portions 113 and 139 are angled so as to converge near tips thereof and pass entirely through and slightly outward of the vertebra 114 so as to secure a hold therein and provide bicortical purchase at opposite ends.

The lateral connector head 106 has an internal bore 141 which is aligned to receive the rod 107, but is ovate and slightly bigger in cross-section in comparison to the rod 107. The wall 128 has approximately the same radius and curvature as the rod 107 so as to snugly receive the rod 107 when urged against the wall 128 by a second set screw 145. As opposed to the hook of the previous invention which does not entirely encircle the rod of that embodiment, the bore 141 does completely encircle the rod 107.

The head 106 has a second somewhat smaller bore 143 with a threaded interior wall 144 that is aligned perpendicularly with respect to the bore 141 and to the rod 107 in use. The bore 143 receives the second set screw 145 which is very similar to the set screw 122 having a base 147 with a threaded exterior surface 148. Initially, the set screw 145 also has a break-away head (not shown) which is broken from the base 147 at a predetermined torque during installation exposing a pair of removal slots 149. The set screw 145 has a lower axially aligned point 150 that engages the rod 107.

The present invention is utilized in a manner that is similar to the previous embodiment in order to anchor at least one end of the rod 107. A similar system can be utilized at the opposite end of the rod 107 or therealong, if necessary, to secure the rod 107. The rod 107 is held during use by the set screw 122 in the bone screw 112 and by the set screw 145 in the lateral connector 105. The lateral connector 105 in turn is rigid and joins with the second bone screw 137 which is laterally offset from the bone screw 112, so as to increase the ability of the implant system 101 to anchor the rod 107 and resist forces acting on and through the rod 107, especially rotational forces. The two part anchor formed by the combination of the bone screw 112 and the lateral connector 105 with the bone screw 137 provide resistence to rotation of the rod 107, axial movement of the rod 107 and inadvertent dislodgement of the implant 101 from the vertebra 114.

Figures 10, 11, 12, 13:
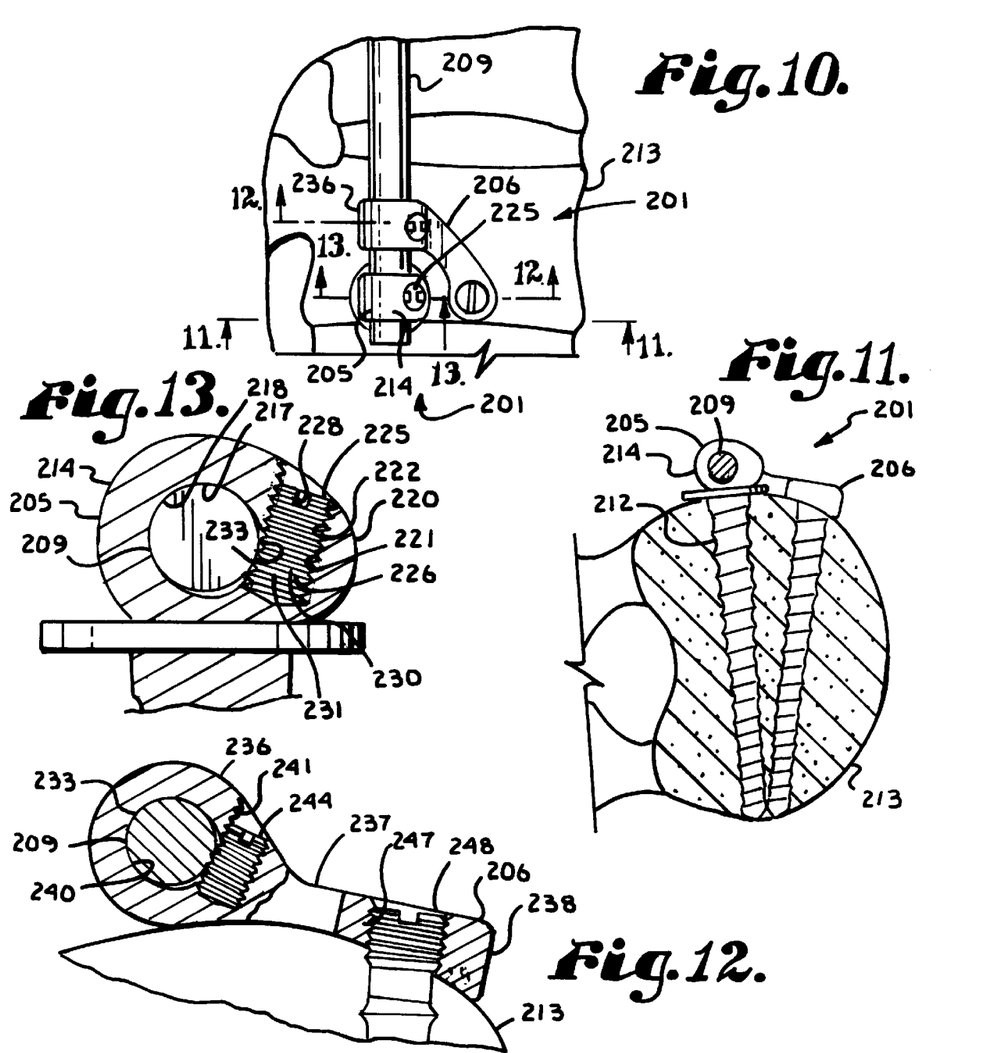
FIG. 10 is a fragmentary front elevational view of a second modified anchor in accordance with the present invention, in association with vertebrae and a rod.
FIG. 11 is a cross-sectional view of the second modified anchor, associated vertebra and rod, taken along line 11—11 of FIG. 10.
FIG. 12 is an enlarged cross-sectional view of the second modified anchor, associated vertebra and rod, taken along line 12—12 of FIG. 10.
FIG. 13 is an enlarged cross-sectional view of the second modified anchor, associated vertebra and rod, taken along line 13—13 of FIG. 10.

Illustrated in FIGS. 10 through 12 is a third embodiment of an anchor implant system in accordance with the present invention, generally represented by the reference numeral 201. The implant system 201 is in some aspects similar to the implant system 1 and 101 of the previous embodiments and, consequently, certain details thereof which are similar in nature will not be reiterated herein.

The implant system 201 includes a first bone screw 205, a lateral connector 206 within which is mounted a second bone screw 207. A rod 209 is operationally secured and held by both the bone screw 205 and the lateral connector 206.

The bone screw 205 has a lower threaded portion 212 that is threadably received in a vertebra 213 in use. The bone screw 205 also has a head 214 that extends outwardly from the vertebra 213.

The bone screw head 214 has a first bore 217 that extends perpendicularly with respect to the bone screw threaded portion 212. The bore 217 is sized slightly bigger than and to slidably receive the rod 209 therein with the rod 209 snugly received against one side wall 218.

The bone screw head 214 is enlarged on one side thereof so as to form a shoulder 220 within which a second bore 221 is positioned that is very carefully sized, shaped and located so as to open into the first bore 217 and so as to have one side that is located slightly radially inward of a tangent of the rod 209 when fully assembled. The bore 221 has an internal threaded surface 222.

A first set screw 225 is sized and shaped to be received in the bore 221. The set screw 225 has a base 226 and initially a head (not shown) that breaks from the base during installation once the set screw 225 has reached a predetermined torque. Slots 228 are located in the base 226 and are accessible only when the head (as in previous embodiment) breaks away therefrom, so as to allow insertion of a tool (not shown) access for removal, should such be necessary. That is, slots 228 allow grasping of the base 226 within the bore 221 to rotate the base 226 and remove it therefrom.

The base 226 has an external threaded surface 230 with a series of threads 231 thereon. The set screw 225 and the bore 217 are sized, shaped and positioned in such a manner that, as the set screw 225 is advanced, the set screw 225 first urges the rod 209 against the side wall 218 of the first bore 217 opposite the set screw 225 and, thereafter, passes somewhat radially inside of the tangent of the rod 209 in the bore 221.

Because the set screw 225 is radially inward of an outer surface 233 of the rod 209, the threads 231 cut into the surface 233 so as to penetrate the rod 209. Once the set screw 225 is fully advanced in the bore 221, a torque begins to develop as the set screw 225 is turned. Once a predetermined torque is reached, the head 227 breaks from the base 226 leaving the base 226 in the bore 221 and securing the rod 209 in the head 214. In this manner and especially because the set screw threads 231 physically cut into and remain lodged in grooves in the rod 209, the set screw 225 very effectively resists rotational movement of the rod 209 relative to the bone screw bore 217, while also resisting axial movement of the rod 209 within the bone screw bore 217.

The lateral connector 206, see FIG. 12, has a closed head 236, a laterally extending arm 237 and a tail 238. The connector head 236 has an interior bore 240 sized and shaped to slidingly receive the rod 209 therein. A second bore 241 is positioned to extend slightly radially inward of a tangent of the rod 209, as does the second bore 221 of the bone screw 205 previously described. The second bore 242 threadably receives a set screw 244 therein. The set screw 244 is essentially the same type as the first set screw 225 and functions in the same manner. In particular, the second set screw 244 also engages and cuts into the outer surface 233 of the rod 209 so as to both urge the rod 209 against the opposite side of the bore 240 and to cut into and resist rotation of the rod 209 within the bore 240.

The connector tail 238 also includes a third bore 247. Threadably received in the third bore 247 is a second bone screw 248. The second bone screw 248 is positioned by the lateral connector 206 so as to be located perpendicularly or radially outward from the rod 209 relative to the first bone screw 205.

The implant system 201 of the present embodiment is used in the same manner as the previous embodiments to secure a rod 209 either at one end, at both or intermittently therealong against both movement axially along the rod and rotationally about the rod, while resisting dislodgement of the implant 201 from the bone 213.

Figure 14:
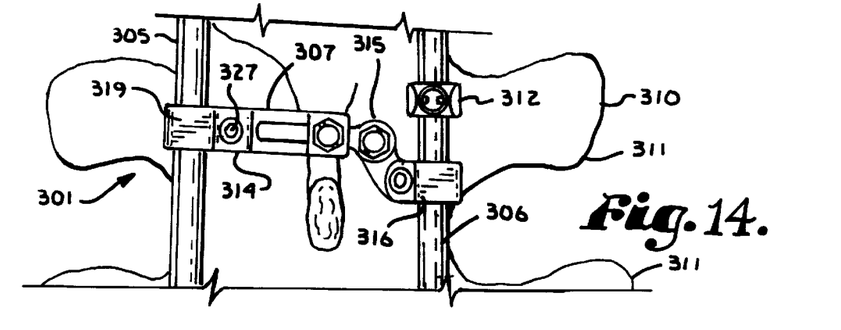
FIG. 14 is a rear elevational view of an implant system including a pair of rods, a connector and a spine associated with an implant of the system.
Figure 15:
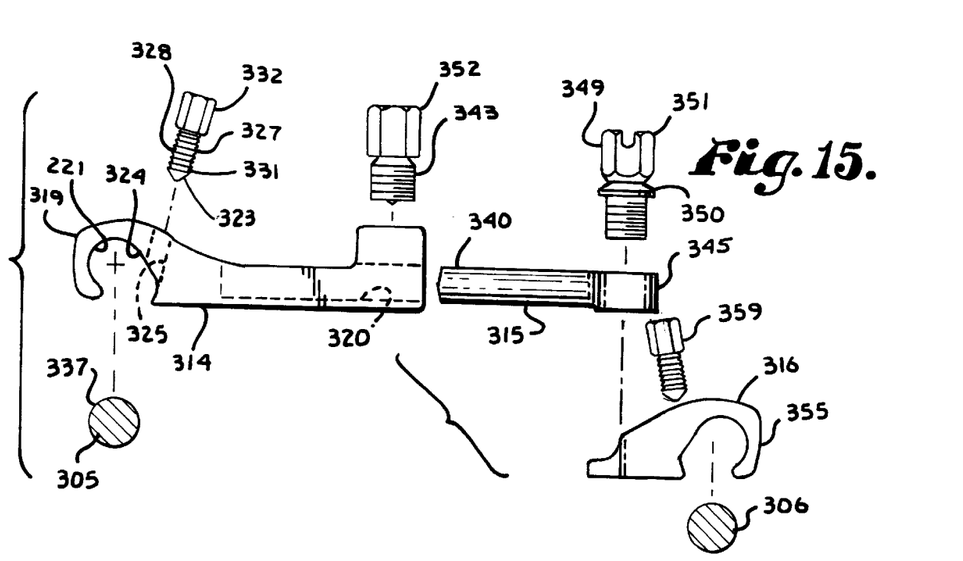
FIG. 15 is an exploded view of the implant system of FIG. 14 prior to installation.

Illustrated in FIGS. 13 through 15 is a fourth embodiment of an implant system in accordance with the present invention, generally identified by the reference numeral 301. The implant system 301 has a different intended usage in comparison to the implant systems 1, 101 and 201 of the previous embodiments, but incorporates some of the same rotation resisting features thereof. In particular, the implant system 301 incorporates use of a set screw to resist both axially movement and rotation of rods used in medical implants relative to the rest of the implant. The system 301 is used to provide connection between pairs of rods 305 and 306 that are positioned on opposite sides of a spine 310.

In particular, the implant system 301 includes the pair of elongate rods 305 and 306 and a lateral connector 307 that spans or passes over the central structure on the rear of the spine 310. The present embodiment illustrates use of aspects of the present invention in conjunction with medical implants that differ from the anterior rod implant system of the previous embodiments. In particular, the present implant system includes the pair of rods 305 and 306 which are laterally spaced and are positioned to be secured to and pass along opposite sides of the posterior of the spine 310. The rods 305 and 306 are joined by bone screws, such as screw 312, or other implants (not shown) to vertebrae 311 of the spine 310. In order to help secure the position of the rods 305 and 306 and stabilize the rods 305 and 306, a lateral connector 307 is utilized, as shown in FIG. 13.

The lateral connector 307 has a body member 314, an arm 315, and an offset hook 316. The body member 314 is elongate with a hook 319 located at one end thereof and a circular bore 320 extending axially therealong from an opposite end. The hook 319 is sized and shaped to be received over rod 305 with a curved wall 221 to receive the rod 305. A bore 323 is sized, located and shaped so as to intersect with an interior 324 of the hook 319. The interior of the bore 323 has a threaded surface 325.

A first set screw 327 is received in the bore 323 and has a threaded outer surface 328 which is sized and shaped to be received and threadably advanced along the bore surface 325. Located at the base of the bore 323 is a wall 329 against which the set screw 323 sets after installation, such as is shown in FIG. 15. The set screw threaded surface 327 is located on a lower base 331 thereof and the set screw 327 also has an upper head 332 that breaks from the base 331 when a preselected torque is achieved, such as is shown in FIG. 15. The set screw base 331 also includes a pair of upper slots 333 that are located and positioned to allow a removal tool (not shown) to be inserted into the slots 333 once the head 332 breaks away from the base 331 to allow rotation of the base 331 by the tool.

The set screw 327 is inserted in the bore 323 during installation of the implant system 301 while the rod 305 is in the hook 319. The set screw 327 first urges the rod 305 against the hook interior 324 and in particular against a surface 335 opposite the bore 323. The set screw 327 and bore 323 are positioned such that the set screw 327 engages the rod 305 slightly radially inward from an outer surface 337 thereof, such that the threads of the threaded surface 328 must physically cut into the rod outer surface 337 and create grooves therein within which certain of the threads of the threaded surface 328 remain seated subsequent to insertion of the set screw 327. Once the set screw 327 is fully installed against the wall 329, a torque develops as the set screw 327 is continued to be rotated and once a preselected torque is achieved, the head 332 breaks from the base 331, leaving the base 331 in the bore 323.

Figure 16:
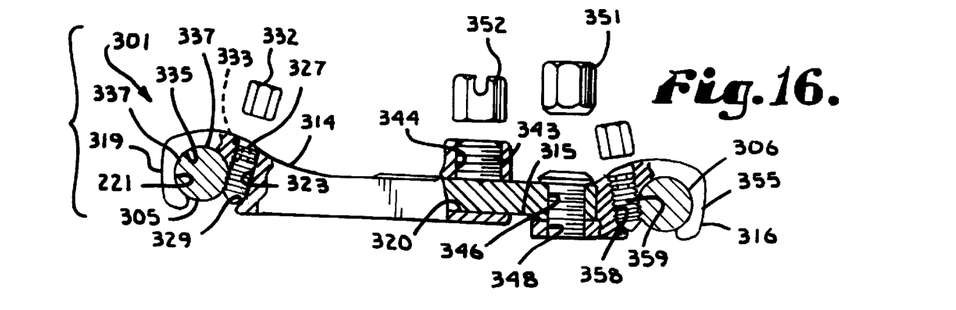
FIG. 16 is a bottom plan view of the implant system of FIG. 14 subsequent to installation showing heads of various set screws removed and illustrating utilization of a locking set screw in accordance with the present invention for securing and locking the rods relative to the connector.

The arm 315 has an elongate section 340 that is generally circular in cross-section and which is snugly but rotatably received in the body member circular bore 320. In this manner, the arm 315, when not yet secured and locked can both reciprocate and rotate within the circular bore of the body member 314 so as to allow for proper positioning of the various elements of the implant system 301. Once the arm 315 is considered to be properly positioned with respect to the rest of the implant system 301, a set screw 343 is inserted into a threaded bore 344 of the body member 314 to secure the arm 315 in a selected position, such as is seen in FIG. 16.

The arm 315 also has a loop 345 at the end opposite the elongate section 340 which includes an internal bore 346. The offset hook 316 also includes a bore 348 that is threaded and which is sized, shaped and positioned in use beneath the bore 346 and which receives a third set screw 349 therein. The third set screw 349 has an upper flange 350, as the bore 346 is not threaded and the flange 350 properly locates or positions the set screw 349 within the bore 346 during use. The set screws 349 and 343 both have heads 351 and 352, respectively, that break away during installation after a preselected torque is achieved, so as to provide a low profile construction to the remaining portions of the set screws 349 and 343.

The offset hook 316 has a hook element 355 positioned opposite the bore 348. The hook element 355 is sized and shaped to be received over the rod 306 in the same manner as the hook 319 is received over the rod 305.

The offset hook 316 also has a second bore 358 that receives a set screw 359. The set screw 359, bore 358 and position of the rod 306 effectively function in usage in the same manner as the set screw 327 with respect to bore 323 within which the set screw 327 is received, so as to secure the rod 306 from both axial and rotational movement relative to the lateral connector 307, once the entire system is installed such as is shown in FIG. 15.

The implant system 301 is utilized to provide support to a spine 310 to allow a patient to use their back subsequent to an injury, a disease or the like that has damaged or deformed the spine 310 in such a manner so as to make the back unusable or cause severe pain or produce substantial deformity. The rods 305 and 306 are joined to the spine 310 by various bone screws (such as screw 312) or other implant structures which are well known in the art. The lateral connector 307 is then utilized to join together the rods 305 and 306 thereon and to provide stability and support to the rods 305 and 306. The present invention is especially directed to the use of the set screws 327 and 359 to secure the rods 305 and 306 in the lateral connector 307 and prevent both axial movement and rotational movement of the rods 305 and 306 relative to the lateral connector 307.

It is foreseen that the present invention can be used in a wide variety of implants wherein either a rod needs to be anchored securely or wherein it is desirable to prevent both axial and rotational movement of the rod relative to the implant. The present invention can be used in conjunction with both open implants such as hooks or closed implants such as the enclosed heads shown in certain of the embodiments.

It is to be understood that while certain forms of the present invention have been illustrated and described herein, it is not to be limited to the specific forms or arrangement of parts described and shown.

What is claimed and desired to be secured by Letters Patent is as follows:

1. An implant system for use in conjunction with a bone structure in a living body; said system comprising:
   a) an elongate rod sized, shaped and adapted to be positioned to extend along the bone structure;
   b) an anchor for operably securing said rod to the bone structure; said anchor comprising:
      i) a first bone screw adapted to be set in said bone structure; said first bone screw secured to said rod during use;
      ii) a second bone screw adapted to be set in said bone structure; and
      iii) an offset connector; said connector being secured to said second bone screw and said rod during use; said connector being sized and shaped so as to position said second bone screw in spaced relation to both said rod and said first bone screw on a common side of the bone and such that said second bone screw is laterally positioned relative to said rod from the location whereat said first bone screw is secured to said rod.

2. The implant system according to claim 1 wherein:
   a) said second bone screw is positioned generally radially from said first bone screw relative to said rod.

3. The implant system according to claim 1 wherein:
   a) said connector is sized and shaped to rest upon and be supported by the bone during use.

4. The implant system according to claim 1 wherein:
   a) said connector includes a hook and wherein said rod is received in an opening of said hook; said connector further including a set screw have a treaded portion for securing said connector to said rod;
   b) said hook opening configured to include an interior surfaced shaped to snugly receive a portion of said rod; said set screw being positioned opposite said hook surface in use; said set screw also being positioned such that as said set screw is advanced during installation, said set screw initially urges said rod against said surface and thereafter said set screw threaded portion engages and partly cuts into said rod near a tangent of said rod such that the set screw both locks said rod in said hook and also resists rotation of said rod relative to said hook.

5. The implant system according to claim 1 wherein:
   a) said connector includes a head having a rod receiving bore that is sized and shaped to slidingly receive said rod; said head including a second threaded set screw receiving bore;
   b) a set screw sized and shaped to be threadably received in said bore; and
   c) said rod receiving bore and said set screw receiving bore being positioned and aligned such that when said rod is in said rod receiving bore and said set screw is fully advanced in said set screw receiving bore, said set screw has external threads thereon that are positioned radially inward of a tangent of the rod, such that said threads cut into and remain positioned in the rod subsequent to assembly.

6. An implant adapted to be secured to a rod in use; said implant comprising:
   a) an implant body having an opening for receiving a rod in said opening and an internal surface facing a portion of an outer surface of the rod in said opening;
   b) a threaded bore extending into said body and intersecting on one side thereof with said opening; said bore being positioned opposite said opening internal surface; and
   c) a set screw threadably received in said bore; said set screw having a base with a threaded surface; said bore being positioned and aligned, such that when the rod is in the opening and said set screw is advanced in said bore, said set screw initially urges the rod against the bore interior surface opposite the set screw and thereafter said set screw threaded surface engages and cuts into the rod surface such that after said set screw is operationally set, said set screw threaded surface continues to engage the rod and resist rotation of: the rod in said opening.

7. The implant according to claim 6 wherein:
   a) said implant body is a hook.

8. The implant according to claim 6 wherein:
   a) said opening is a rod receiving bore that encircles the rod.

9. A medical bone implant anchor for anchoring a rod to a bone; said implant comprising:
   a) a first bone screw adapted to be secured to the rod;
   b) a lateral connector adapted to be secured to the rod; and
   c) a second bone screw secured to said lateral connector and being spaced laterally with respect to said first bone screw.

10. In a set screw system wherein a set screw is positioned in a bore during use and has external threads; said set screw setting a rod relative to an implant; the improvement comprising:
   a) said set screw bore opening onto said rod and said set screw bore being located radially inward of a tangent of the rod so that said set screw initially urges said rod against said implant during installation and then said set screw threads cut into a rod surface and remain in the rod after the set screw is set.

11. A medical implant comprising:
a) a first element having a threaded bore and a receptacle;
b) a second rod member element operably secured to said first element while received in said first element receptacle during usage; and
c) a set screw with exterior threads operably threadedly received in said bore; said bore being aligned and spaced with respect to said receptacle such that when said set screw is fully advanced in said bore, said set screw threads generally tangentially engage and grip said rod member, so as to resist rotation of said rod member.

* * * * *